United States Patent [19]

Blomberg

[11] Patent Number: 4,617,016
[45] Date of Patent: Oct. 14, 1986

[54] INJECTION DEVICE

[76] Inventor: Anders Blomberg, P1 6238 Höglanda, S-434 00 Kungsbacka, Sweden

[21] Appl. No.: 518,805
[22] PCT Filed: Dec. 13, 1982
[86] PCT No.: PCT/SE82/00423
 § 371 Date: Jul. 19, 1983
 § 102(e) Date: Jul. 19, 1983
[87] PCT Pub. No.: WO83/02062
 PCT Pub. Date: Jun. 23, 1983

[30] Foreign Application Priority Data

Dec. 14, 1981 [SE] Sweden .............................. 81074585

[51] Int. Cl.$^4$ ............................................. A61M 5/20
[52] U.S. Cl. .................................. 604/155; 604/407; 604/414; 128/DIG. 1
[58] Field of Search ................. 604/154–155, 604/68, 71–72, 407, 414; 128/DIG. 1

[56] References Cited

U.S. PATENT DOCUMENTS

| | | | |
|---|---|---|---|
| 3,395,704 | 8/1968 | Frey et al. | 604/154 |
| 3,701,350 | 10/1972 | Guenther | 128/DIG. 1 |
| 3,720,211 | 3/1973 | Kyrias | 604/155 |
| 4,108,177 | 8/1978 | Pistor | 128/DIG. 1 |
| 4,273,122 | 6/1981 | Whitney et al. | 604/155 |
| 4,405,318 | 9/1983 | Whitney et al. | 604/155 |

*Primary Examiner*—C. Fred Rosenbaum
*Assistant Examiner*—Michelle N. Lester

[57] ABSTRACT

Injection device for medical purposes, designed for injection by using a manual hypodermic syringe. It includes a barrel part which in one end has a syringe needle and in the other end a flange; a plunger part having a plunger displaceable in the barrel part, said plunger performing movements, enabling medicine to be sucked into and respectively injected from the barrel portion, and having a gripping part connected with the plunger by means of a plunger rod. The device has an opening in one end, through which the injection syringe can at least partly be introduced into a cavity, and an inner part which is provided with a holding device for the barrel part which is changeable between a releasing position and a holding position, in which the barrel portion is held against movements in its longitudinal direction relative to the inner part. A displacement device is provided for displacing the plunger part between a fore and a rear displacement position. The inner part is changeable between a rear position with the syringe needle positioned inside the opening and an advanced position with the syringe needle pushed outside the opening for insertion. The injection device includes an outer part, in which an electric motor is positioned and controlled by means of an electronic device. A transmission connects it to the displacement device for accomplishing its displacement movements in a sequence determined by the control device, for loading the injection syringe, as well as injection after insertion.

7 Claims, 15 Drawing Figures

INJECTION DEVICE

BACKGROUND OF THE INVENTION

The present invention refers to an injection device for medical purposes, designed for injection by means of a manual hypodermic syringe. It includes a barrel part which at one end has a syringe needle and at the other end a flange, and a plunger part having a plunger displaceable in the barrel part. The plunger is capable of performing movements, enabling medicine to be sucked into and respectively injected from the barrel part and has gripping means connected with the plunger by means of a plunger rod. The injection device has an opening, through which the injection syringe can at least partly be introduced into a cavity, and an inner part which is provided with a holding device for the barrel part.

When treating certain diseases it is required that the patient regularly, often daily, be supplied with medication by injection. One such disease is diabetes, affecting many people. It is important that these patients be able to inject themselves with insulin. However, complications are connected with this disease, and blindness is one of them. Many of the insulin dependent diabetics also have other additional diseases, which complicate the insulin injections, for instance a slight hemiplegia, rheumatism, or Parkinson's disease. The fact that the frequency of diabetes also increases with age makes loading and injection of insulin with a conventional hypodermic syringe a great problem.

The majority of diabetics use a completely manual hypodermic syringe, a so-called disposable hypodermic syringe. A blind or handicapped person has considerable difficulty in filling such a syringe with the prescribed amount of insulin and then inserting the needle into the skin followed by injection. An aid in the form of an injection gun is known; however, it only takes care of the inserting part. There are also some aids for loading but they are considered too impractical by patients.

It is an object of the present invention to provide an injection device with which loading, as well as inserting and injecting, can be accomplished without any demands being placed on the user's sight or manipulation ability.

BRIEF SUMMARY OF THE INVENTION

The object is achieved by means of an injection device according to the present invention, which is characterized in that it comprises a holding device which is changeable between a releasing position and a holding position, in which the barrel part is held against movements in its longitudinal direction relative to the inner part; and in that it also comprises a displacement device for displacing the plunger part in two directions relative to the barrel part between a fore and a rear displacement position, the arrangement being such that the fore displacement position is a releasing position for the plunger part. In the remaining displacement positions it is in a position to bring the plunger part to both displacement positions. The inner part is changeable between a rear position, with the syringe needle positioned inside said opening, and an advanced position, with the syringe needle pushed outside said opening in order to insert the needle into body tissue. The injection device includes an outer part, in which an electric motor is positioned and controlled by means of an electronic control device. The electric motor is by means of a transmission mechanism connected to the displacement device, for accomplishing its displacement movements in a sequence determined by means of the control device for loading the injection syringe, as well as for insertion and injection.

BRIEF DESCRIPTION OF THE DRAWINGS

The invention will now be described with reference to the enclosed drawings, in which.

DETAILED DESCRIPTION OF A PREFERRED EMBODIMENT

Figure 1:
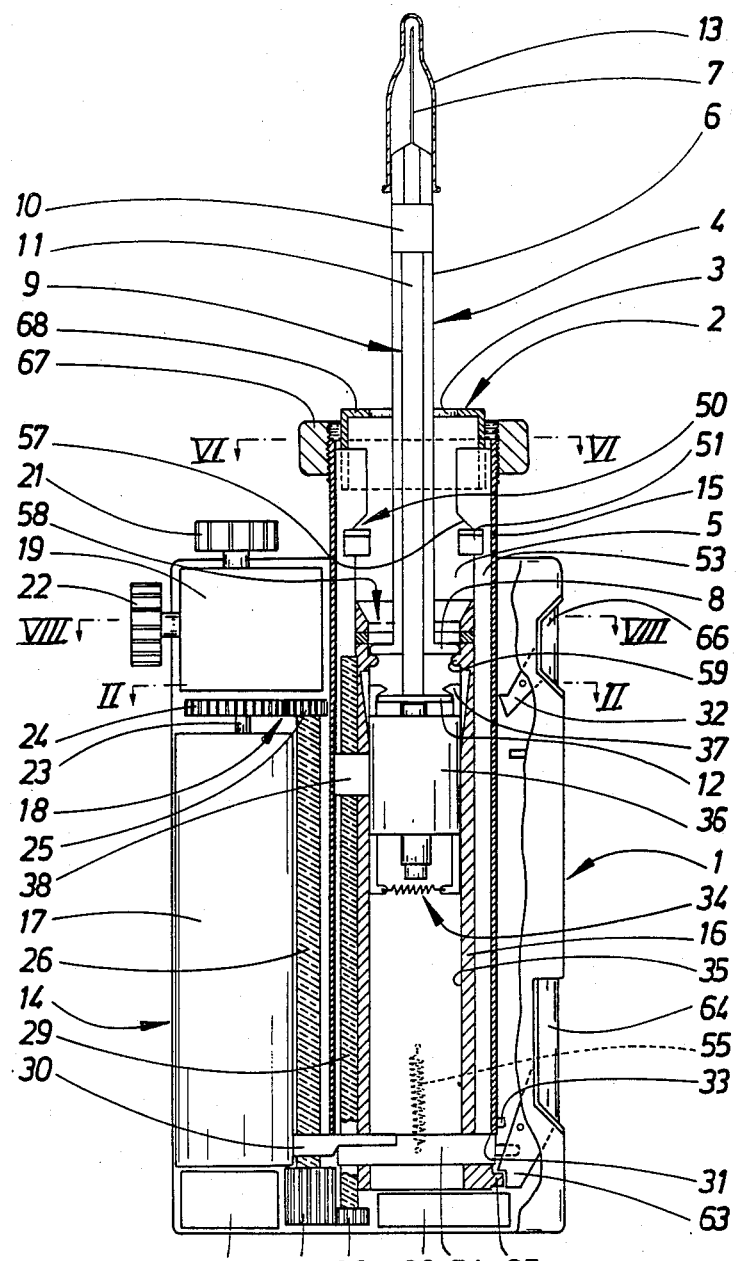
FIG. 1 shows a view, partly in section, of the injection device according to the invention, with an attached disposable hypodermic syringe.
Figure 2:
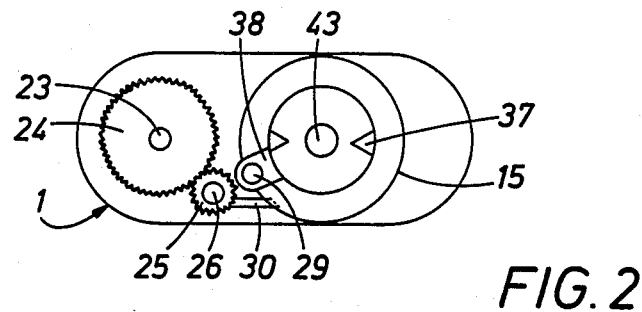
FIG. 2 is a schematic section along the line II—II in FIG. 1 of the injection device.

In FIGS. 1 and 2 the principal construction of the injection device 1 is shown. In its upper part 2 it comprises an opening 3, through which a hypodermic syringe 4 of a disposable type can be introduced, into a cavity 5 in the injection device. The disposable syringe is of a standard type and mainly consists of a barrel part 6 which forms a cylindrical part and in its upper part has a syringe needle 7 and in its rear part is provided with a flange portion 8 in the form of two laterally directed flanges. The disposable syringe 4 furthermore has a plunger part 9 consisting of a plunger 10, a plunger rod 11, and a gripping plate 12, situated at the outer end of the plunger part. The gripping plate 12 is connected to the plunger 10 which is movable inside the syringe 4 in order to aspirate or respectively push medical material through the syringe needle 7. The syringe needle is protected by a detachable top cover 13 attached to the barrel part 6. The injection device 1 is built up of three main parts which are movable relative to each other, viz. an outer part 14, which forms a housing for the injection device, a middle part 15 movable relative to the housing and a movable inner part 16, movable relative to the middle part 15, by e.g. ½ to 1 cm.

The disposable syringe 4 is held in the inner part 16 in a manner which will be further described below. The housing 14 has a cylindrical bore as a guide for the middle part 15, out of which the middle part can be pulled to an extended position, which will also be described more closely in the following. In the housing 14 there are, besides the middle part 15 and the inner part 16 with attached inner parts, an electrical motor 17 and the main parts of a transmission 18 for achieving at least some of the working movements of the injection device.

Furthermore, the housing 14 encloses an electronic control device 19, made to control the motor 17 according to certain predetermined sequences, in a manner which will be more closely described in the following. In the bottom of the housing 14 there are accumulators 20 supplying the motor 17 and the control device 19 with electric current. On the housing 14 there are also two adjustable wheels 21, 22 for adjusting two different amounts of liquid medicine to be injected. For the sake of simplicity it is assumed in the present embodiment that the medicine is insulin, of which certain patients require two different kinds to be loaded into the syringe. The amount of insulin of one kind is set by the wheel 21 and the amount of insulin of the other kind is adjusted by the other wheel 22.

Figure 13:
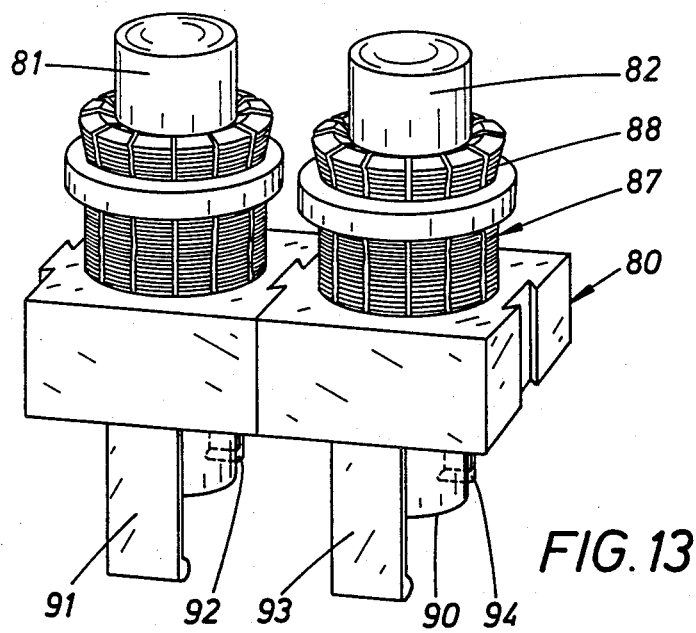
FIG. 13 shows a perspective view of a bottle holder for two injection bottles.
Figure 14:
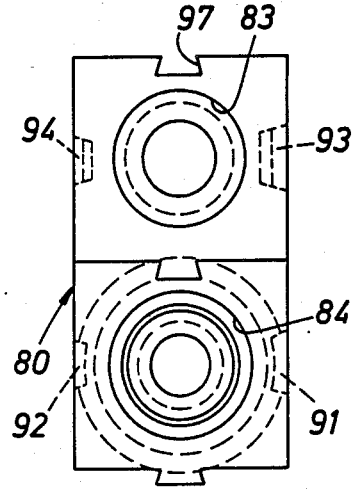
FIG. 14 is a top view of the bottle holder.
Figure 15:
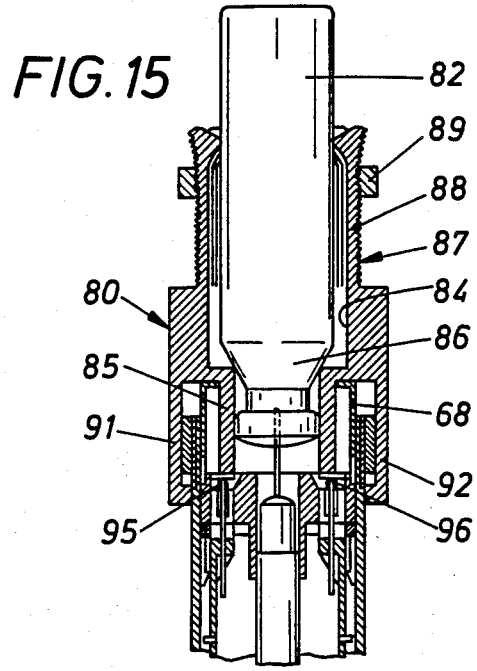
FIG. 15 is a section through the bottle holder attached to the upper end of the injection device.

For the sake of simplicity, in the description of FIGS. 1 and 10-12, one case is indicated when there is only one sort of insulin, while FIGS. 13, 14 and 15 show a case with two sorts of insulin. The wheel 22 that is intended for the other sort can for example be set in a zero position. The electrical motor is in the example shown a D.C. motor with a rotating terminal shaft 23, which extends parallel with the moving directions of the middle part 15 and the inner part 16. The D.C. motor 17 can be provided with a capsulated gear train (not shown) for gearing down of the rotations of the motor. The transmission 18 is constituted of a pinion 24 on the output shaft 23 of motor 17 and a pinion 25 in meshing engagement with the pinion 24 and fixed on one end of a threaded shaft 26, which has a rotating bearing in the housing 14 and at its other end a pinion 27 of a relatively large width. This pinion 27 is in meshing engagement with another pinion 28 fixed on the end of a screw shaft 29 which is threaded in the same direction as the driving shaft 26. The screw shaft 29 has a rotating bearing in the wall of the inner part 16. The driving shaft 26 is connected to a driving joggle 30 which has a bore with internal threads and is guided in a slot not shown in the inner part 16 through which the driving joggle 30 is made to move along the driving shaft 26 when the driving shaft is rotating. The driving joggle 30 acts on an edge, e.g. the lower edge 31 of the middle part or tube 15 in order to lift it while moving upwards and to displace the middle part 15 in the direction out of the housing 14 to an outer position shown in FIGS. 11 and 12. In the outer position it is hooked with a spring-loaded pawl 32 having a rotatable bearing in the housing 14. The pawl is brought to act on a projecting portion 33 on the tubular middle part 15. When the driving shaft 26 is caused to rotate in the opposite direction, which makes the driving joggle move downwards, the middle part 15 remains in its outer position.

The inner part 16 has a displacement device 34 for the gripping plate 12 of the plunger part 9. The displacement device 34 is displaceable in a bore 35 of the inner part 16 between a fore position shown in FIG. 10 and a back position shown in FIG. 11. The displacement device 34 consists of a mainly cylindrical body 36 to which two gripping means are rotatably attached. They are made to hold the gripping plate 12 and take it along during the displacement movements of the displacement device.

Figure 3:
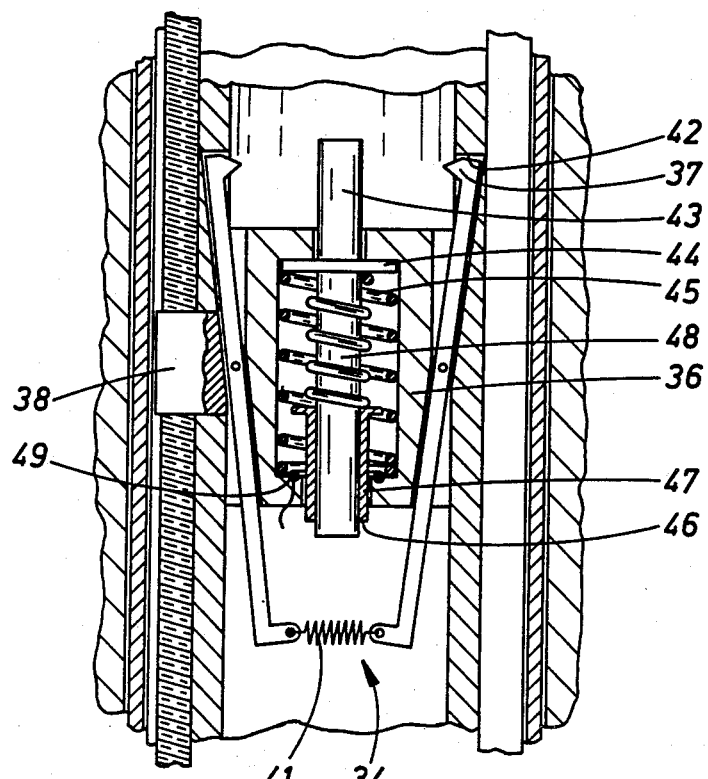
FIGS. 3 and 4 show, on a larger scale, a partial view of a mechanism in the injection device for displacing the plunger part of the disposable hypodermic syringe in two different positions.
Figure 4:
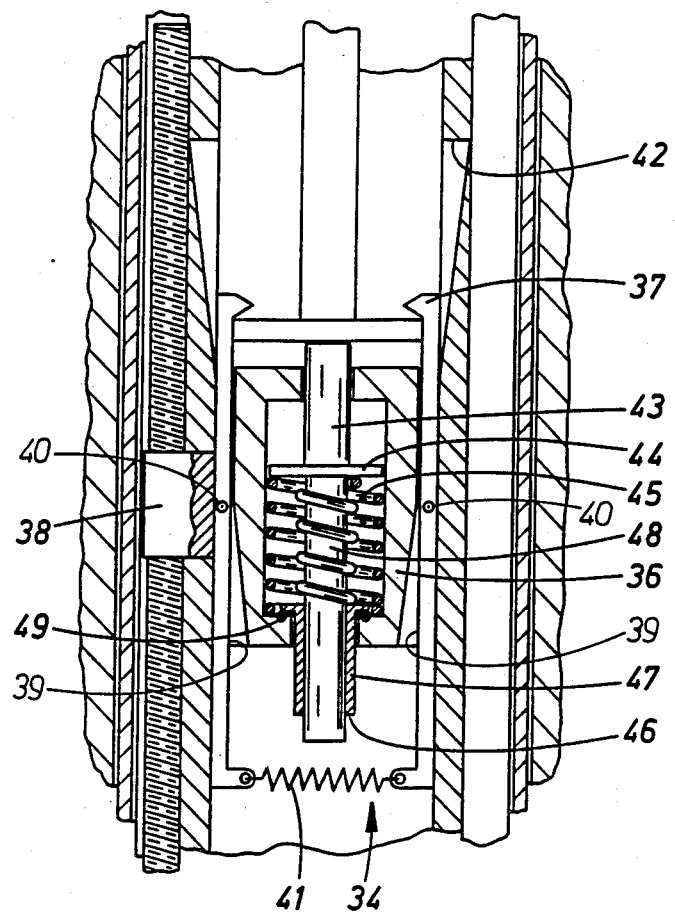

The construction of the displacement device 34 is best shown in FIG. 4, showing a broken partial view of the injection device on an enlarged scale. In FIG. 3 the displacement device 34 is shown in its fore end position, in which the gripping means 37 is positioned in a releasing position and in FIG. 4 in a somewhat displaced position in which the gripping means 37 is in a holding position for the gripping plate 12, and in this way the gripping means are positioned during the displacement movements of the displacement device except for the position shown in FIG. 3. The displacement movements of the displacement device are achieved by rotation of the screw shaft 29 acting on a nut 38 or more precisely a bore internally threaded, projecting as a part from the cylindrical body 36. The gripping means 37 are each positioned in a groove 39 in the cylindrical body and each one has bearings with its own pivot 40 in the cylindrical body. The two grooves 39 are successively enlarged over the pivot 40 in order to let the gripping means 37 perform a tipping movement through the action of a tensioning spring 41 connecting the two gripping means with each other below the cylindrical body. As the inner part 16 in its wall has two widenings 42 positioned opposite to each other and intended to take up the gripping means 37 in the fore end position of the displacement device 34, the change of the gripping means to a releasing position is made possible by means of the tension spring 41. As shown in FIGS. 3 and 4 the cylindrical body has a pin 43 with a flange 44 and a coil spring 45 extending upwards in order to hold the pin 43 in the position shown in FIG. 3 in which the gripping plate 12 will be held essentially without play in the hooking position of the gripping means 37. In the lower part of the pin 43 a metal socket 47 is pressed against a projection 46, whereby contact of an electric circuit is achieved with a contact strip 49 against the metal socket 47, without this contact action being a stop position for the pivot 43, which is thus able to be pressed down a little further when contact has been achieved between the metal socket 47 and the contact strip 49. This forms the main switch for the control device 19 and the motor 17. The switch is in a releasing position when the hypodermic syringe 4 is removed from the injection device, but in an on-position according to FIG. 4 when the hypodermic syringe is in place with the gripping plate 12 pressing down the pin 43.

Figure 5:
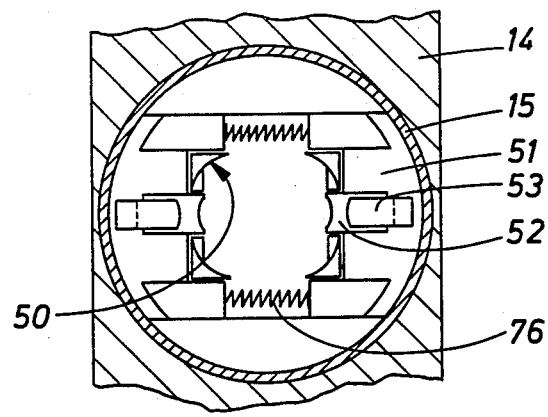
FIGS. 5 and 6 show a supporting mechanism for the disposable hypodermic syringe located in the upper part in the injection device, in two different positions, in a view along line VI—VI in FIG. 1.
Figure 6:
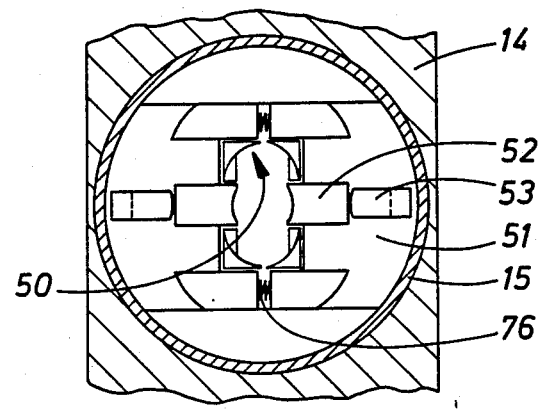
Figure 11:
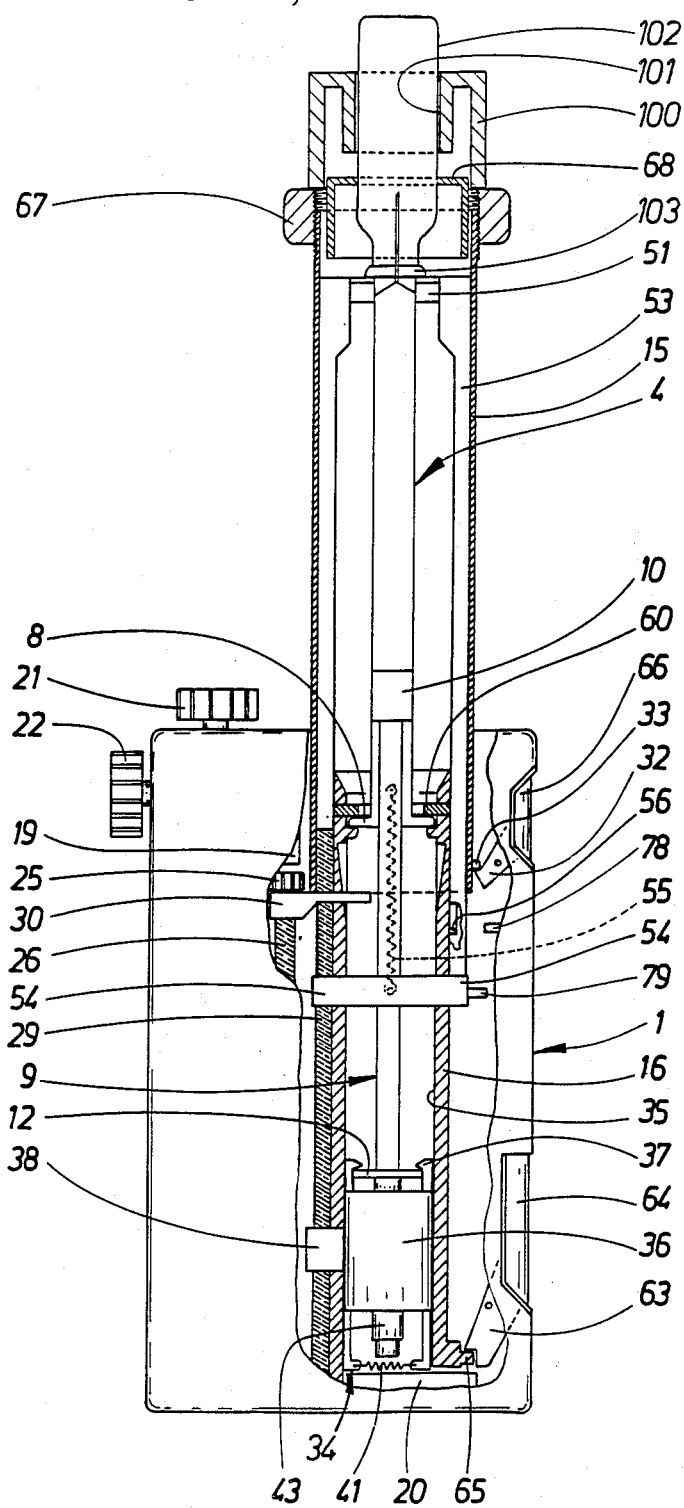
FIG. 11 shows the hypodermic syringe after having been inserted into body tissue but prior to injection.
Figure 12:
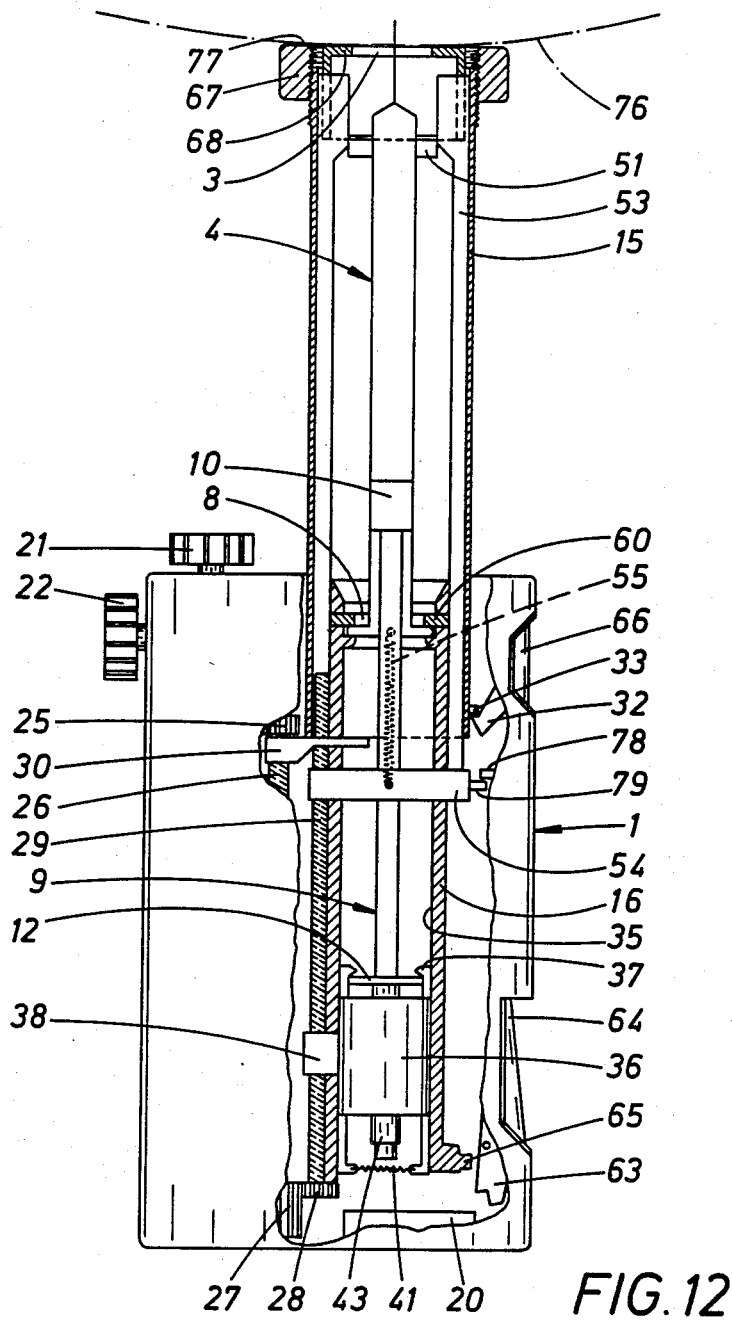
FIG. 12 shows the hypodermic syringe after insertion into body tissue and during injection.

The injection device 1 further has an upper supporting means 50 located in the middle part 15, some distance down from the opening 3. The supporting means 50 is intended to form a support for the hypodermic syringe 4 in its upper part, and thus to center it in the cavity 5 of the injection device, and to automatically lift off the needle protection 13 before the syringe is loaded. The location of the supporting means is shown in FIGS. 1 and 11 and its construction in FIGS. 5 and 6. The supporting means 50 are changeable between a retracted position shown in FIGS. 1 and 5, and a protruded supporting position shown in FIGS. 6, 11 and 12. In the retracted position the hypodermic syringe can be put in place into the injection device, while in the protruded supporting position the hypodermic syringe is centered and gets support on its sides. However, the hypodermic syringe 4 is not held but is able to make a displacement movement relative to the supporting means 50. This is done during the moment of insertion, to be described later on. The supporting means are made of two supporting elements 51 which are movable from and towards each other in grooves on the inside of the tube-like middle part 15. The two supporting elements 51 have in between them two coil springs 76, striving to keep the supporting elements from each other in the retracted positions. On the upper side of the supporting elements there are situated two metal strips 52, intended to be part of an electrical circuit to be described later on. Included in the supporting means are also two long expansion means 53 in the form of electrically conductive bars which are electrically insulated from the tube-like middle part 15 and other parts of the device too. The two expansion means 53 extend all the way down to the lower part of the injection device in the position shown in FIG. 1 and are fixedly connected to a spring ring 54, which is displaceable within the bore of the housing 14 relative to the housing, as well as to the middle part 15 and the inner part 16. The spring ring 54, however, is connected to the middle part 15 by two tension springs 55, of which one is shown in FIG. 1. By this arrangement the ring 54 is made to follow the outward movement of the middle part 15 during the main part of its displacement, but is hooked by a hooking element 56 in the inner part 16 and remains in the position shown in FIG. 11, so that the two tension springs 55 are stretched during the last part of the displacement of the middle part 15. As indicated in FIG. 11, in a partly broken view of one expansion means 53, they have an impact area which will be hooked against said means. When doing so the expansion means 53 are stopped in their displacement movements, through which the middle part 15 and thus also the supporting elements 51 move relative to the expansion means. As each of these expansion means at their upper ends are made with an obliquely angled guiding area 57, this relative movement will press the two supporting means 51 inwardly against the action of coil springs 52 to the supporting position shown in FIGS. 6 and 11, whereby the needle protection 13 thus is pressed upwards and through this will be lifted up, and the hypodermic syringe will be stabilized and centered.

Figure 7:
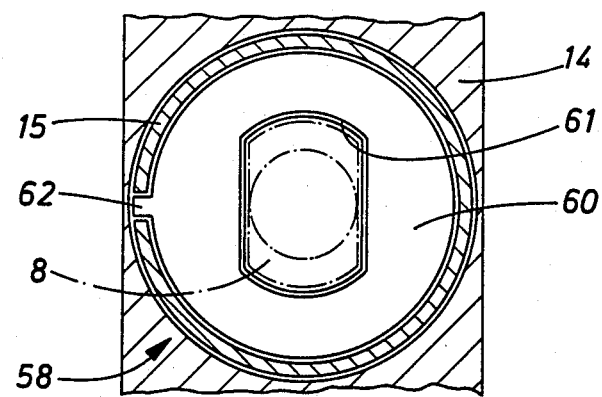
FIGS. 7 and 8 show a section through the injection device along the line VIII—VIII in FIG. 1, showing a holding means for the body of the disposable syringe.
Figure 8:
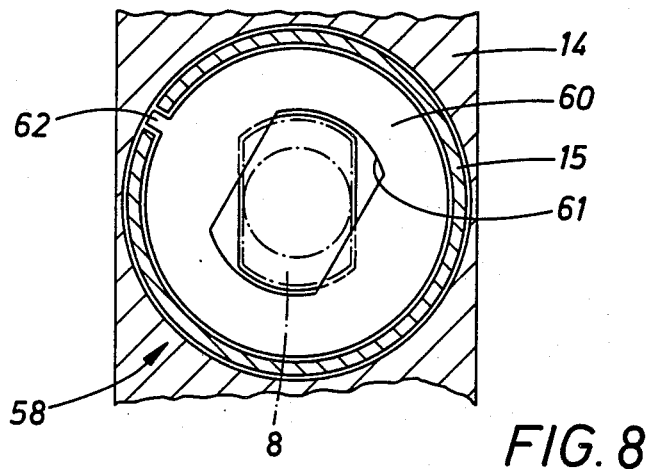

A holding means 58 for the barrel part 6 of the hypodermic syring is arranged further upwards in the inner part 16. Holding means 58 is made of a narrowed part of the inner part 16 which forms stopping means 59 against which the hypodermic syringe 4 is put in place with its two laterally directed flanges in the flange portion 8. Also the holding means 58 is provided with a stopping means in the form of a twist ring 59, which can rotate in the inner part 16. The construction of the holding means 58 is best shown in views of FIGS. 7 and 8. FIG. 7 shows the holding means in a releasing position, and FIG. 8 in a holding position. A twist ring 60 has a central hole 61 which mainly corresponds to the form of the portion of the barrel part 6 of the hypodermic syringe with the two flanges in the flange portion 8, and somewhat exceeds the dimensions for these. Through this the flanges are permitted to be placed on the stopping means 59 and situated on a level located under the twist ring 60. The twist ring has in its periphery a guide screw 62, which penetrates in a long obliquely formed perforation in the tubular middle part 15.

The height of the perforation corresponds to the total displacement distance of the middle part. In the releasing position shown in FIG. 7 the hole 61 of the twist ring 60 coincides with the stopping means 59 for the flange portion 8. By displacement of the tubular middle part 15 relative to the housing 14 of the injection device a twisting motion of the twist ring 60 occurs, since the inner part 16 and thus also the twist ring 60 will not join in the outward pulling movement and the guide screw 62 will be guided in the perforation in the middle part. As soon as this motion begins an edge portion defining hole 61 will be moved over the flange portion 8 of the barrel part of the hypodermic syringe, thus causing the barrel part of the hypodermic syringe to be held in the inner part 15.

Returning to FIG. 1, it shows that the inner part 16 will be held in a position in FIG. 1 by a pawl 63, which has a rotatable bearing in the housing 14 and can be activated from the outside against action of a spring by a trigger 64. The pawl 63 cooperates with an inner edge 65 on the outside of the inner part 16 as long as the trigger 64 is not pushed. The upper pawl 32 has a similar trigger 66, which can be pushed in against action of a spring for releasing the pawl 32, which happens when the middle part 15 shall be brought back to its retracted position. This will be done manually after the injection device has performed its operations. Also the injection device has on the upper portion of the middle part 15 an adjustable ring 67, which is threaded on the middle part 15 and can be adjusted to different heights by rotation, for changing the insertion depth of the syringe. Inside said ring 67 is a top cover 68 which defines the opening 3 of the injection device and has a spring acting on it so that it strives to maintain the top position shown in FIG. 1, but can be pushed down as long as the hypodermic syringe is located in its inner position. When pushing down the top cover 68 an electric circuit is closed in order to activate motor 17 for injection, this being achieved by contact strips or a microswitch located in the top cover 68.

Figure 9:
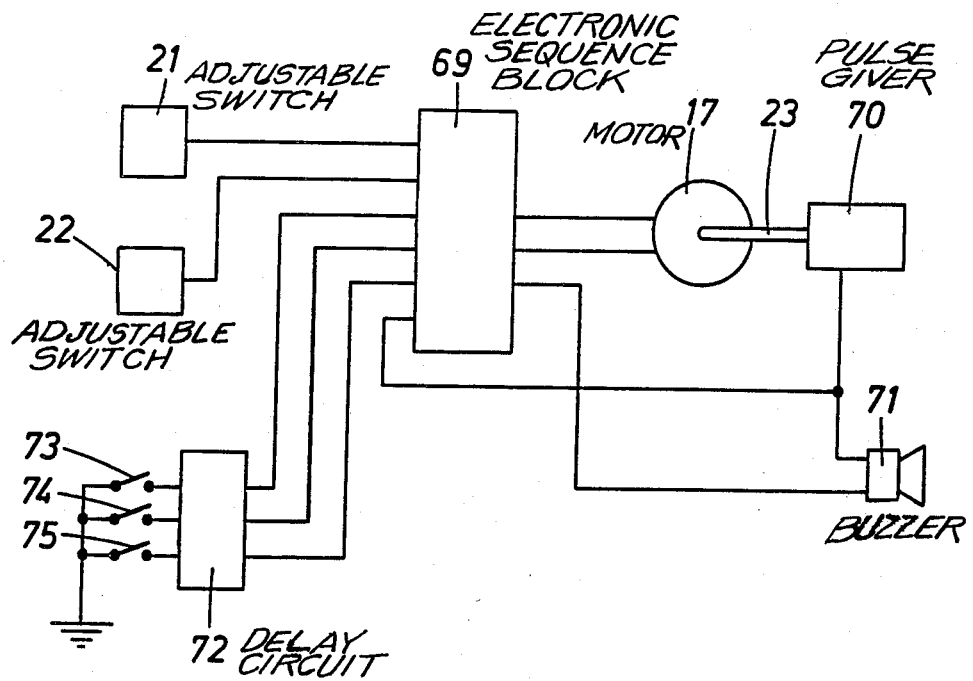
FIG. 9 shows schematically a block diagram of an electronic controlling device forming a part of the injection device.

FIG. 9 shows schematically the construction of the electronic control device 19 for controlling the electrical motor 17. Adjustable switches 21 and 22 are for example thumb-wheel switches which are connected to inputs of an electronic sequence block 69 which can be constructed according to conventional digital techniques. It can activate the electrical motor 17 for rotating its output shaft 23 in one or the other direction during a predetermined time in order to perform all the working movements. The motor 17 has a feed-back control, e.g. an optical pulse giver 70, which feeds back information of the number of revolutions of the motor and consequently of performed work. The optical pulse giver 70 is so constructed with a frequency divider that the feed-back signal is divided down to a frequency that corresponds to a certain amount of pulses for every unit of insulin, e.g. one pulse per unit. The insulin dosage is viz. in number of units, thus four units correspond to one tenth of a millimeter, this usually called a line, since the hypodermic syringes are graded in such lines. To the sequence block 69 and the feed-back circuit there is connected also a buzzer 71, which marks the amount of units that are sucked in during the loading movement, e.g. every fourth unit. To the input side of the sequence block 69 are three switches 73, 74 and 75 connected via delaying and adapting circuits 72. The three switches 73, 74 and 75 are situated in the injection device in order to start certain actions through mechanical activation. One switch 73 has been mentioned earlier and is situated in the displacement means 34 and is put into "on" position by putting in the hypodermic syringe 4, more exactly by pressing down the pin 43 with the gripping plate 12. The second switch 74 is put on "on" when the displacement means 34 is in its back position and can be made as a microswitch or the like. The third switch 75 has also been mentioned above and has been designed to close the electrical circuit by the expansion means 50 or when the top cover 68 is pushed in and when the trigger 64 is pulled simultaneously, which activates the motor 17 for injection. The sequence block can for example be made of a four-bit counter and counts positions (10-15) to be decoded with an exit 16 demultiplexer. Each of these exits represents a time phase in the working cycle. They will control the motor via logic circuits. One counter is also arranged for every adjustable switch and is counted down to zero from the set value.

Figure 10:
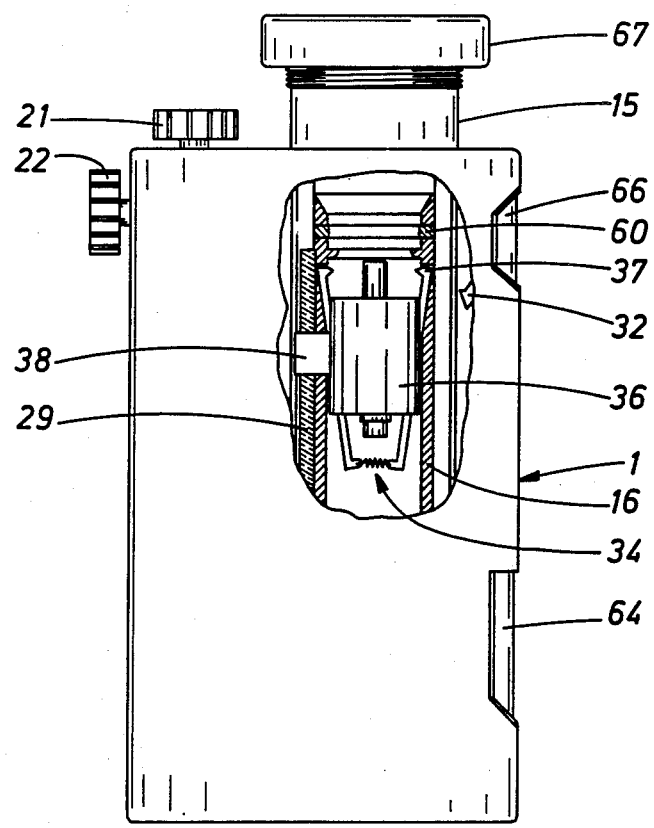
FIG. 10 shows a view, partly in section, of the injection device in an initial position before the disposable hypodermic syringe has been inserted into the injection device.

With reference to FIGS. 1, 10, 11 and 12 the different actions of the use of the displacementt device 1 will now be described. The initial position of the injection device is shown in FIG. 10 before any hypodermic syringe has been put into the device. At this stage the tubular middle part 15 is in a totally retracted position and the driving joggle 30 thus in its lower position.

The displacement means 34 is in its upper position at this moment, thus gripping means 37 is in its releasing position (see FIG. 3). Since the middle part 15 is in its inner position, the holding means 58 also is in a release position and the supporting means 50 in retracted position. All three switches 73, 74, 75 are at this moment in open position. When a hypodermic syringe 4 is put into the injection device through the opening 3, when its flange portion 8 comes into contact with the stopping means 59 (see FIG. 1), the pin 43 is pressed down in the displacement means 34 (see also FIG. 4), thus closing switch 73. At this moment the motor 17 is started in such a direction, that the driving joggle 30 is displaced upwards at the same moment as the displacement means 34 moves downwards. At the same moment the gripping means 37 change at once to a holding position through the movement of the displacement means 34, bringing with it the gripping plate 12 backwards and the plunger 10 to be displaced downwards. FIG. 1 shows this position when the tubular middle part 15 has been lifted some distance by the driving joggle 30 and the displacement means 34 is moved some distance downwards. That the plunger follows and the displacement means 34 moves downwards in the first movement has, however, no functional importance, since the loading action has not yet begun. This first movement has for its only purpose to bring along the long expansion means 53 and the ring 54 with the tension spring 55. Some distance before the upper end position of the middle part 15 the expansion means 53 are hooked and thus also the ring by the hooking part 56 on the inner part 16 (see FIG. 11), this making the ring and the expansion means to stop in their upward going movement, while the middle part 15 continues on. Upon this movement the two supporting elements 51 of the supporting means 50 are changed from their retracted position to their protruding positions in order to center the hypodermic syringe through cooperation with the oblique edges 57 of the expansion means 53. During the pushing out movement of the middle part 15 the displacement means 58 is also changed from its releasing position to its holding position, according to FIG. 8. In its outer position the middle part 15 is hooked by the pawl 32 and remains thus in this position. In this end position the switch 74 is activated, causing the control means 19 to activate and switch the rotating direction of the motor 14.

The switch 74 can for instance be situated in the bottom of the inner part 16 and activated by the displacement means 34 which at this moment is in its lower end position, according to FIG. 11.

At this moment the displacement means 34 moves back to its fore position shown in FIG. 10, which is the starting point of the loading movement. This begins with the displacement means 34 moving downwards to a position that corresponds to the preset insulin volume, set by wheel 21. A mainly circular detachable bottle holder 100 is put above the top cover 68 and has a round opening 101, through which an insulin bottle 102 turned down can be put inside in order for the hypodermic needle 7 to penetrate the rubber membrane in the end of the bottle. At this moment the switch 75 is closed, which for example may consist of the two metal strips 52 mentioned earlier and the metallic top 103 at the membrane of the insulin bottle 102. For practical reasons, however, this may be replaced by a microswitch or something similar because of the fact that not all bottles have an electrically conductive surface. At this moment the control means 19 is activated in order to start motor 17, causing the displacement means to move upwards to its upper end position. Thus, the insulin bottle 102 will be filled with an amount of air corresponding to the amount of insulin to be injected, which creates a favorable excess pressure. When the displacement means 34 has reached its fore position and thus also the plunger its upper position, the rotation direction is changed, after which the displacement means 34 is pulled down to a position that corresponds to the present insulin volume plus additional volume corresponding for example to two units, after which it turns back and stops in a position corresponding to the preset volume. During this movement insulin is sucked in and any possible enclosed air will be ejected, as shown in FIG. 11. The preset amount of insulin thus is now in the hypodermic syringe 4.

The loading action has now been finished, thus the insulin bottle 102 and the bottle holder 100 will be pulled away and the adequate depth of insertion is set by the adjustable ring 67 for setting the insertion depth. After this the injection device is pushed against the body tissue 76 where the insulin is to be injected, while the top cover 68 is pressed in against action of its coil spring, to a depth such that the top of the adjustable ring 67 rests against the skin. The device is now ready for insertion, which occurs by pulling the trigger 64, upon which under action of the tension springs 55 the inner part 16 together with the hypodermic syringe 4 is inserted until the spring ring 54 moves into its upper end position, which is determined by a contact 78 with which a portion 79 of the spring ring 54 cooperates (see FIG. 12). The hypodermic syringe with its needle thus penetrates to the necessary depth and through closure of the switch 75, which is achieved when the top cover 68 is pushed and the trigger 64 is pulled at the same time, injection occurs, that is, the motor 17 displaces the displacement means 34 and accordingly the plunger 10 of the hypodermic syringe 4 forward in such a way that the enclosed amount of insulin will be injected into the body tissue. At the same time the buzzer 71 can ring if desired. When the plunger 10 has reached its end position and all of the amount of insulin has been injected, the injection device is withdrawn and is placed on its previous place. The driving joggle 30 is at this moment in its lower end position, making it possible to release the middle part 15 from its hooked position by pushing the upper pawl 61. The middle part can manually be pushed inside the housing 14, in which position the barrel part 6 of the hypodermic syringe 4 will be released from its holding position, all done in a similar manner as has been previously described, but in the opposite direction. The gripping means 37 has also been changed to a releasing position, making also the gripping plate free so that the hypodermic syringe can be totally withdrawn from the injection device.

According to a favorable way of carrying out the invention, the top cover 68 also acts as a safety contact in order to prevent insertion of the injection device to occur when not intended. If injection is to occur the trigger must be pulled and the top cover must be pushed down at the same time. A twisting disc is situated in the top cover over the upper portions of the expansion means 53 as long as the top cover is not pushed inwardly. This safety function can only be cancelled by a circular movement made by pushing in the top cover at which an oblique edge of the top cover acts on the twisting disc in order for the twisting disc to twist when the top cover is pushed in. At this moment, a notch in the twisting disc will be situated at the middle of each upper end of the expansion means, in order to make it possible for the expansion means to be freely displaced upwards and injection can occur.

As mentioned above for the sake of simplicity, loading and injection of one kind of insulin only has been mentioned. Principally the injection device works in a similar manner when two kinds of insulin are used. In this case, the two dosages are set by the adjustable switches 21 and 22. Sucking in air in the hypodermic syringe occurs up to a volume corresponding to the total amount of insulin, that is the sum of the amount of insulin for both kinds of insulin. The two kinds of insulin are provided each in an insulin bottle of which the first is placed in the upper part in the injection device, and the injection of air occurs corresponding to the amount of insulin for the first kind of insulin. After this the first bottle is withdrawn and the other bottle is attached. Then air corresponding to the amount of insulin for the other kind of insulin is injected in the corresponding bottle. Then the set amount of insulin is sucked into the hypodermic syringe from the second bottle, after which the bottle is withdrawn, and the first bottle is put on. The amount of insulin for the bottle of insulin is after this sucked into the hypodermic syringe from the first bottle, which then is withdrawn and the device is ready to inject in exactly the same manner as in the example described above.

The bottle holder shown in FIGS. 13, 14 and 15 for the bottles 81 and 82 with two kinds of medicine, e.g. two different kinds of insulin, facilitates the loading procedure especially for blind people, since no error can happen, provided only that the bottles are in the right place in the bottle holder. This bottle holder 80 has two cylindrical through-going cavities 83, 84 made to enclose one bottle each. This cavity has a portion 85 narrowing in steps, designed to form a support for the narrowing portion 86 of the bottle. Furthermore, a tubular portion 87 projects from the body of the bottle holder 80 in each cavity. This projecting portion 87 has external threads and is slotted in order to create many elements 88, that in their upper ends have a narrowing diameter. Each tubular portion 87 is surrounded by a ring 89, through which each bottle 81, 82 can be cramped by screwing up the ring after the bottles have been inserted. The stepwise narrowing part 85 of the cavity has an annular supporting area 90 facing downwardly. By virtue of this supporting area the bottle holder can rest against a supporting area facing upwardly in the upper end of the injection device, as shown in FIG. 15. From this it is evident that also in this example an injection device with a slightly divergent construction is shown, compared with other figures. The narrowing part 85 of the holder 80 is so designed that it can project into the opening of the top cover 68 and thus get support from its edge area. The holding ability of the bottle holder 80 is achieved also by four downwardly projecting hooking means 91, 92, 93 and 94.

In a similar manner the upper portion of the injection device is formed with two notches, designed to fit two hooking means at a time, that is either the hooking means 91, 92 or the hooking means 93, 94 depending on the bottle 81, 82 that is meant to be used during the loading procedure. The two hooking means 91, 92 and 93, 94 respectively have different dimensions for each bottle. In a corresponding way the notches in the upper part of the injection device have different dimensions. Through this arrangement each bottle can be attached only in one way, which is important. The third switch that has been described earlier is in this case replaced by two switches 95, 96 (FIG. 15) which are designed to close a circuit each through by contact with any conducting part of the device. The two switches 95, 96 could for example be connected to each one of two extensions 93, at which the bottle holder 80 has another contact part that for example is situated in the ring-shaped supporting area 90 and is designed in a different way for each of the holding parts of the two bottles. The contact parts in the holder 80 are so situated that when attaching one bottle, that is the narrowing part 85, the switch 95 is activated, but when attaching the other bottle the other switch 96 is activated. This can for example be arranged in such a way that the supporting area 90 has over a portion thereof an electrically conducting cover, that reaches along the outside of the narrowing part 85 and achieves contact with for example an electrically conductive part of the top cover, and through this activates the electrical control device 19 in a way that loading takes place up to the right amount of insulin. At the narrowing part 85 for the other bottle the electrically conductive layer is placed at another part of the projecting surface 90 so that the other switch 96 will be activated and closing another circuit of activation of the electrical control for loading of the other kind of insulin.

The holder 80 for the two bottles 81, 82 is thus used in a way that first the bottle holder 80 is placed in a way that one bottle 81 will be situated right above the upper part of the injection device so that the hypodermic syringe can penetrate into the bottle and loading can occur with the first kind of insulin. After this, the holder 80 is withdrawn and moved away so that the other bottle 82 of insulin will be situated right above the hypodermic syringe and loading can occur with the other dosage of insulin. The two switches 95, 96 are arranged in a manner such that at the moment of injection the top cover 68 will in a similar way as mentioned above close an electrical circuit in order to start the injection action through activation of the electrical control device.

The invention is not limited to the examples described and shown above in the drawings, but can be varied within the scope of the following claims. For example, it is possible that the electronic part, that is the control device 19 and the accumulators 20 are placed in a unit separate from the device and connected with the other part through a flexible cable. It is furthermore possible that the pulling out action of the middle part 15 is not performed by the electrical motor, but can be done totally manually, so that the motor thus only performs the displacement movements for the displacement device 34.

Under these circumstances one threaded shaft is sufficient and the driving joggle 30 is left out. It is also possible that the electric motor is of a linear type and situated in the bottom, with the driving shaft coaxial with the middle part and the longitudinal axis of the inner part.

The insertion depth can be achieved in a different manner, for example through an adjustable screw that determines the lower end position for the top cover by stopping the top cover against the upper part of the screw. The holding means can be replaced by means that are movable radially from the wall of the inner part, e.g. pins or something similar.

I claim:

1. An injection device for medicine, comprising: an outer part forming a housing, and an inner part reciprocably supported in said outer part, said inner part having an opening and a cavity in communication with said opening; and an injection syringe having a barrel part having a first end and a second end, a syringe needle at said first end and a flange at said second end, a plunger part in said barrel part and having a plunger displaceably mounted in said barrel part for sucking medicine into said barrel portion and for injecting medicine from said barrel part, said injection syringe extending through said opening at least partly into said cavity, said inner part having a holding device for the barrel part, said holding device having means movable between a releasing position in which said barrel part is reciprocable in said cavity and a holding position, in which said barrel part is held against movement in said inner part, said inner part also having a displacement device operatively connected to said plunger part and movable relative to said holding device in two directions relative to the barrel part, between a fore and a rear displacement position, said displacement device having gripping means movable between a releasing position and a gripping position and operable to release said plunger part in said fore displacement position of said displacement device and to grip the plunger part in other positions of the plunger part, said inner part being movable in said outer part between a rear position in which said syringe needle is positioned inside said opening and a fore position in which the syringe needle is outside said opening for insertion into body tissue, said injection device including a bottle holder positioned at said opening for positioning at least one medicine bottle for loading of said syringe, during which the syringe needle is inserted into a medicine bottle in said bottle holder and a predetermined amount of medicine is sucked into the barrel part, said injection device including an electric motor positioned in said outer part, an electronic control device in said outer part and operatively connected to said motor, and a transmission connecting said electric motor to said displacement device for effecting said displacement movements of said plunger part in a sequence determined by said control device, for loading the injection syringe and for injecting medicine into the body tissue.

2. An injection device according to claim 1, further comprising a tubular intermediate part positioned between said inner part and said outer part and displaceable between a retracted position and an extended position relative to said inner part and said outer part, a spring mechanism connected between said inner part and said intermediate part, means for tensioning said spring mechanism upon movement of said intermediate part and for moving the inner part with the injection syringe a distance from a rear position to a fore position, said outer part including a trigger mechanism having a releasable pawl cooperating with said inner part for locking said inner part in said rear position of said inner part and for releasing said inner part from said rear position to said fore position of said inner part.

3. An injection device according to claim 2, wherein said intermediate part has a top portion and includes supporting means positioned in said top portion, said support means being displaceable in the retracted position of the intermediate part into a removed position and in the extended position of the intermediate part to be in a forward supporting position for the barrel part.

4. An injection device according to claim 2, further comprising straining means connected to the support means for following during part of the movement of the intermediate part.

5. An injection device according to claim 4, wherein said spring mechanism is connected to said straining means.

6. An injection device according to any one of claims 1 to 5, wherein said gripping means includes stopping means and hooking means cooperating with a guide surface in said inner part for changing over between the gripping and the releasing position of the plunger part.

7. An injection device according to any one of claims 1 to 5, wherein said holder is capable of holding at least two medicine bottles and further including means for coupling said holder adjacent to said opening so that insertion of the needle takes place into one bottle at a time, means for sensing the position of the holder, and means for activating said control device for loading the syringe with a preset amount of medicine from each of said at least two bottles.

* * * * *